(12) United States Patent
Valdivieso Cacique et al.

(10) Patent No.: US 8,880,145 B2
(45) Date of Patent: Nov. 4, 2014

(54) PLANNING SYSTEM FOR INTRAOPERATIVE RADIATION THERAPY AND METHOD FOR CARRYING OUT SAID PLANNING

(75) Inventors: Manlio Fabio Valdivieso Cacique, Tres Cantos (ES); Carlos Guillermo Illana Alejandro, Tres Cantos (ES); Manuel Desco Menendez, Madrid (ES); Javier Gonzalez-Garzon Pascau, Madrid (ES); Felipe Manuel Calvo, Madrid (ES); Juan Jose Vaquero Lopez, Madrid (ES)

(73) Assignee: GMV Aerospace and Defence S.A. (ES)

( * ) Notice: Subject to any disclaimer, the term of this patent is extended or adjusted under 35 U.S.C. 154(b) by 1057 days.

(21) Appl. No.: 12/937,568

(22) PCT Filed: Apr. 14, 2008

(86) PCT No.: PCT/ES2008/000240
§ 371 (c)(1),
(2), (4) Date: Nov. 2, 2010

(87) PCT Pub. No.: WO2009/127747
PCT Pub. Date: Oct. 22, 2009

(65) Prior Publication Data
US 2011/0052036 A1    Mar. 3, 2011

(51) Int. Cl.
*A61B 5/05* (2006.01)
*A61N 5/10* (2006.01)
(52) U.S. Cl.
CPC ............. *A61N 5/1031* (2013.01); *A61N 5/1038* (2013.01); *A61N 5/1065* (2013.01)
USPC ............. 600/411; 600/407; 600/427; 378/65; 606/4
(58) Field of Classification Search
USPC .......................... 600/407, 427; 378/65; 606/4
See application file for complete search history.

(56) References Cited

U.S. PATENT DOCUMENTS

| 58,778 A | 10/1866 | Conarroe |
| 140,425 A | 7/1873 | McFarland |

(Continued)

FOREIGN PATENT DOCUMENTS

| EP | 1758649 A1 | 5/2009 |
| WO | 9940523 A1 | 8/1999 |

(Continued)

OTHER PUBLICATIONS

International Search Report PCT/ES2008/000240; Dated Jan. 7, 2009.

(Continued)

*Primary Examiner* — Joel Lamprecht
(74) *Attorney, Agent, or Firm* — Cantor Colburn LLP

(57) ABSTRACT

The invention relates to a simulation and planning system for intraoperative radiation therapy and to a method allowing said system to be used for treatment studies, simulation, planning, training and recording, which system generally comprises a central processing unit or computer (1) for management and control and software-based communication with the rest of the devices and the user; one or several monitors or screens (2) for displaying images and peripherals responsible for gathering data relating to the actions performed by said user, a deformation simulation module for the virtual simulation of the deformation produced in the organs and tissues during the process; algorithms for instantly calculating the radiation dose applied during the radiation therapy treatment simulation and means for recording all the activities carried out and generating a full dosimetry report.

16 Claims, 3 Drawing Sheets

(56) References Cited

U.S. PATENT DOCUMENTS

| | | |
|---|---|---|
| 3,987,281 A | 10/1976 | Hodes |
| 4,729,099 A | 3/1988 | Iverson |
| 5,391,139 A | 2/1995 | Edmundson |
| 5,647,663 A | 7/1997 | Holmes |
| 5,651,043 A | 7/1997 | Tsuyuki |
| 6,032,066 A | 2/2000 | Lu |
| 6,201,988 B1 * | 3/2001 | Bourland et al. ............... 378/65 |
| 6,662,036 B2 * | 12/2003 | Cosman ...................... 600/411 |
| 6,792,073 B2 | 9/2004 | Wickerhauser |
| 7,202,486 B2 | 4/2007 | Gentry |
| 7,266,175 B1 | 9/2007 | Romesberg |

FOREIGN PATENT DOCUMENTS

| | | |
|---|---|---|
| WO | 2004009371 A1 | 1/2004 |
| WO | 2006034973 A1 | 4/2006 |
| WO | 2007028237 A1 | 3/2007 |

OTHER PUBLICATIONS

Martina Treiber, et al., "Integration of itraoperative radiotherapy (IORT) dose distribution into the postoperative CT based external beam radiotherapy (EBRT) treatment planing", Medicine Meets Virtual Reality Feb. 2010, IOS Press, 2002, pp. 529-531.

Manuel Desco, MD., "Simulated Surgery on Computed Tomography and Magnetic Resonance Images: An Aid for Intraoperative Radiotherapy" Computer Aided Surgery 2, pp. 333-339 (1997).

Damian Bernard, PhD. "Design Optimization of Intraoperative Radiotherapy Cones", International Journal Radiation Oncology Biology Physics, vol. 55, No. 5, pp. 1446-1457, 2003.

* cited by examiner

PLANNING SYSTEM FOR INTRAOPERATIVE RADIATION THERAPY AND METHOD FOR CARRYING OUT SAID PLANNING

TECHNICAL FIELD

The present invention relates to a simulation and planning system for intraoperative radiation therapy and to the process or method allowing said system to be used for treatment studies, simulation, planning, training and recording, and for the suitable dosimetry estimation which will be used in the radiation therapy.

More specifically, the system is designed to measure, calculate, estimate, control, plan and/or simulate the method of radiation that a patient receives during a specific intraoperative radiation therapy treatment.

BACKGROUND

Radiation therapy is a form of treatment based on using ionizing radiations (x-rays or radioactivity, including gamma rays, electrons and accelerated particles). Said treatment is commonly used today in oncology treatments for curative or palliative purposes.

Radiation therapy is divided into three types according to the distance of the source of irradiation with respect to the object to be irradiated, these types being called external radiation therapy, brachytherapy and intraoperative radiation therapy.

Radiation therapy generally requires a dosimetric analysis (spatial distribution of the dose deposited in the patient) which is carried out from previously obtained computed tomography (CT or CAT, computed axial tomography) images which, when introduced in planning equipment, allow calculating the distribution of the dose from the radiology attenuation information they contain over the tissues in which it interacts.

Specifically, intraoperative radiation therapy (IORT) for which the method and system of the present invention are described, is a technique combining surgery and radiation therapy generally applied in patients with tumors for which surgical resection (extirpation) has been indicated and in patients who have a high risk of recurrence (return of the tumor), and it consist of directly applying a single radiation dose by means of electron beams, the patient being subjected to surgery in order to expose the targeted area and directly apply the radiation to it.

To that end the area to be irradiated is defined in the attempt to protect healthy tissues either by retracting or separating the rest of the surrounding organs that can be moved or by means of protecting the fixed organs with radiation-opaque elements.

Currently, although there are a number of dosimetry planning tools typically used for external radiation therapy and brachytherapy, this is not the case for IORT, in which given its special characteristics, said tools do not exist, leaving the calculation of the dose to be applied once the patient has already been subjected to surgery up to the surgeon or radiation oncologist and their experience, i.e., once said specialist has access to the tumor which is to be removed or reduced, which, as is evident, results in difficulties in the radiation therapy process and limits both its quality and the subsequent patient progress follow-up.

The reasons which prevent the existence of IORT planning and dosage tools are the difficulties due to the need for retracting or separating the surrounding organs during the surgical process, and due to the extirpation of the tissues concerned, which facts contribute to modifying the morphology of the patient with respect to that observed in the preoperative image studies. These modifications are very difficult to estimate beforehand during planning with the information from a preoperative CAT scan. Furthermore, said problem is even more considerable in the case of IORT, because the radiation is based on the emission of electrons, the dosimetry of which is much more dependent on the exact geometric distribution of the tissues than the radiation based on the emission of photons, which is more common in external radiation therapy.

Therefore, said difficulties translate into the following problems when planning:

Before the intervention: it is difficult to estimate the doses that each structure exposed to the radiation will receive.

During the intervention: dosimetry estimations adapted to surgical findings cannot be performed, such that the planning can be modified and how possible surgical approach alternatives would affect the dosimetry can be evaluated.

After the intervention: since quality control images taken during treatment are not available, as is the case of portal imaging (x-ray images acquired for comparison) in external radiation therapy, that would serve as evidence of the patient's situation during the application of the treatment, the process cannot be correctly evaluated and documented.

Additionally, since it is an invasive technique in which a radiation applicator cone is introduced until it reaches the tissues to be irradiated, entry paths must be searched for and suitable positioning on the tumor bed sought.

As stated, until now it was up to the surgeon or radiation oncologist to decide, according to their intuition, medical and surgical experience, and based on the information generated during surgery, on aspects as fundamental as the diameter of the radiation beam applicator cone, the positioning thereof, the angle of its bevel and even the energy of the electrons.

This means that currently in IORT, a prior dosimetry estimation of the radiation that will be applied is not performed with suitable reliability (comparable to that which is currently obtained in external radiation therapy) and nor are the obtained results (complete extent of the tumor bed, radiation of healthy tissue, . . . ) evaluated or recorded, so the possible side effects can neither be explained nor referenced to the patient's medical history.

A professional who wishes to plan a method of IORT therefore needs a tool which allows estimating the distribution of the dose which will be deposited in the anatomical structures determined by said professional as a function of the different possible approaches. From the point of view of the professional who wishes to evaluate the results of an intervention already performed, it is desirable to further know the doses received in the different structures in order to thus explain and/or study the progress of the patient.

The documents existing in the state of the art do not solve these problems because they relate to the external radiation therapy process, as in the case of U.S. Pat. No. 3,987,281, or only to algorithms improving the dose calculation, such as U.S. Pat. No. 4,729,099 or U.S. Pat. No. 6,792,073 for example.

In other cases, different methods improving the planning by optimizing the number of treatment fields, the orientations of the mobile elements or the formation of the radiation beams have been developed, as in U.S. Pat. No. 7,266,175 or U.S. Pat. No. 7,202,486, but they solely and exclusively relate to the planning process and dose calculation in external radiation therapy.

Finally, there are also designs of several radiation beams with independent intensities, as in U.S. Pat. No. 5,647,663, or the integration of image types in the process, either a computed tomography for external radiation therapy, U.S. Pat. No. 5,651,043, or ultrasound in brachytherapy, U.S. Pat. No. 5,391,139, or works on the quality control of the process which try to reproduce the position of the patient during the different treatment sessions, as in U.S. Pat. No. 6,032,066, WO2007028237 or EP1758649, in some cases using radiation detectors to compare the process with the prior planning (U.S. Pat. No. 140,425 and U.S. Pat. No. 58,778).

However, none of the described systems is oriented towards intraoperative radiation therapy because they are systems integrated in the external radiation therapy process which do not allow reproducing the anatomical modifications experienced by the patient during the surgical process, or calculating the dosimetry for electron radiation in that particular situation of the patient.

There is a scientific paper in which some of the inventors collaborated (M. Desco, J. López, F. Calvo, A. Santos, F. del Pozo, P. Garcia-Barreno) "Simulated Surgery on Computed Tomography and Magnetic Resonance Images: An Aid for Intraoperative Radiotherapy". Comput Aided Surg, 2(6):333-339, 1997) which presented only a joint graphic vision of image studies of the patient and isodose curves for electron radiation, without performing any precise dosimetry calculation or allowing a radiation therapy treatment simulation prior to the intervention, i.e., it is simply a work for displaying the isodose curves previously measured in a water phantom superimposed on the non-modified image studies.

BRIEF SUMMARY

The system and method described in the present invention solve all the aforementioned drawbacks as they generally allow training and/or simulating the process of surgery and radiation therapy treatment—including simulating the deformation produced in the organs during surgery and inserting the radiation applicator cone, as well as its interaction with haptic devices—, determining the suitable dose, its distribution throughout the concerned organ, and recording the results in a safe and effective manner.

In other words, the system of the present invention comprises a dosimetry planner/simulator which favors the intraoperative radiation therapy physical-medical and radiosurgical processes.

Generally, the planning system for radiation therapy of the invention comprises at least one central processing unit in which different software packages or modules are executed in order to control and manage all the devices responsible for representing images and touch as well as to gather data relating to the actions performed by the user, simulating an actual surgical procedure; display means for the specialist to view two-dimensional and/or three-dimensional images; a navigator system for locating elements in the three-dimensional space to position the patient and the radiation applicator cone and to adjust it to the pre-planning information; devices for effectively measuring the dose; haptic devices capable of reproducing/simulating the interaction of said radiation applicator with the neighboring tissues in the simulated surgical procedure; and image capture means for documenting the process and checking the tumor tissue remains.

Therefore, the planning system of the invention generally provides support in each of the three IORT planning phases, which are:

a) Pre-Planning Phase:

The user obtains the CAT scan, PET (Positron Emission Tomography) scan or MRI (Magnetic Resonance Image), combining the images in a single image as a result of the central processing unit and the image display means in which said user can select the areas of interest and/or prepare it in order to configure it such that it simulates the scenario that will be encountered in surgery by means of virtual tissue resection and deformation operations.

Based on the resulting image, the system allows the software simulation of inserting the applicator cone in the patient and, in turn, displaying an approximate distribution of the radiation dose received according to the parameters of the applicator cone (diameter, angling, distance to the source of radiation) and of the radiation beam (energy). It further offers the possibility of modifying any of these parameters interactively during said simulation, evaluating different possible scenarios. This operation helps the specialist both in identifying the entry paths towards the tumor and in searching for support surfaces on the tumor bed, further aiding him to have an idea of the homogeneity of the applied dose, of the repercussion on healthy tissues or of the depth of the dose.

The planning system comprises haptic devices for simulating the handling of the applicator cone, which will further have means for providing force feedback to the user in the event of the virtual applicator colliding with the different parts of the patient's anatomy, thus realistically simulating what will be the subsequent surgical operation and allowing foreseeing a large number of contingencies while at the same time, as is obvious, providing fundamental training to subsequently perform said operation on the patient in an optimal manner.

On the other hand, as a result of the central processing unit, the system instantaneously presents an estimation of the dose which will change in real time as the position of the applicator cone changes during the simulation. The specialist can combine this dose information with the data from prior radiation therapy sessions received by the patient such that the record book reflecting the radiation received by the patient over a determined time period is updated, which prevents exceeding the total recommended doses for each type of healthy tissue.

Finally, once the pre-planning stage is validated by the user and before said study moves on to the following intra-planning phase, in which the system has means for generating a more precise version of the dosimetry calculation, for which dose calculation algorithms which more precisely simulate the physical interactions of the electrons can be used.

b) Intra-Planning Phase:

In the intra-planning phase, in the operating room, the system allows, by means of the central processing unit, the radiation applicator cone and the navigator, recording the position of the patient with respect to the accelerator and thus referencing the prior planning data. The system will thus know at all times the position of the applicator and the user can configure the arrangement of the elements of the method, patient and applicator cone as planned. The system allows all the calibration mechanisms necessary so that the error between pre-planning and intra-planning is the lowest possible error. Finally, the user can change planning data according to what is observed during the intra-planning phase.

The system further allows connection to a linear accelerator by means of a communication module in order to be able to supply the data on the dose to be administered.

The system further has optional radiation measurement and image capture means which allow obtaining effective target area radiation data.

c) Post-Planning Phase:

In the post-planning phase, once the treatment is performed the system allows recording all the activities carried out with associated information in a dosimetry report. This report records the parameters of the selected applicator, quantifications of the dose received in areas to be protected and areas to be irradiated, as well as photographs or images of the dose distribution and images obtained in real time by the image capture means.

Additionally, the system allows verifying the data on the planned dose with respect to the actual dose received by the patient using the devices for effectively measuring the dose, which verification will allow establishing a quality measurement of the pre- and post-surgical procedure.

BRIEF DESCRIPTION OF THE DRAWINGS

To complement the description that is being made and for the purpose of aiding to better understand the features of the invention according to a preferred practical embodiment thereof, a set of drawings is attached as an integral part of said description in which the following has been depicted with an illustrative and non-limiting nature.

DETAILED DESCRIPTION

Figure 1:
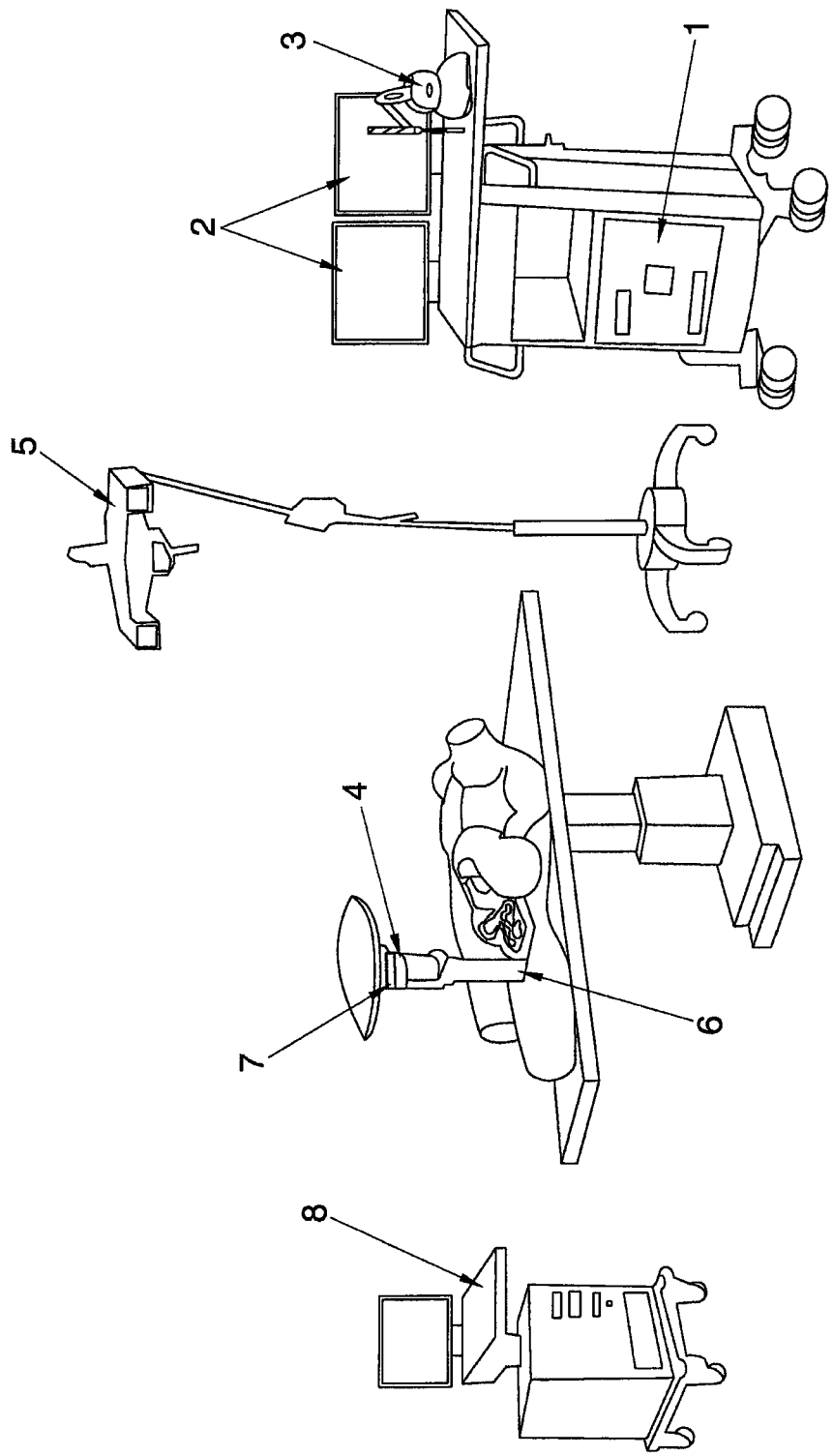
FIG. 1 shows a schematic view of the elements comprised in the system of the invention.
Figure 2:
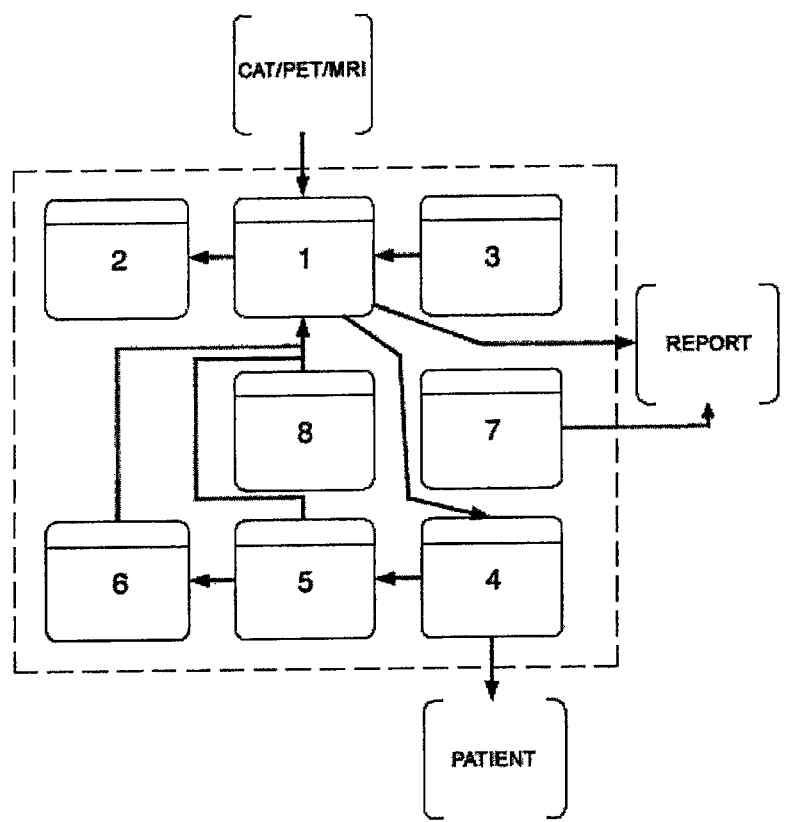
FIG. 2 shows a block diagram of the system of the invention in which the main elements of the system of the invention are indicated, from the images obtained from the patient prior to the treatment to the outputs, which will be the dosimetry report of the planning performed and the application of the dose on the actual patient, in which arrows further show the information flows between each of said blocks.
Figure 3:
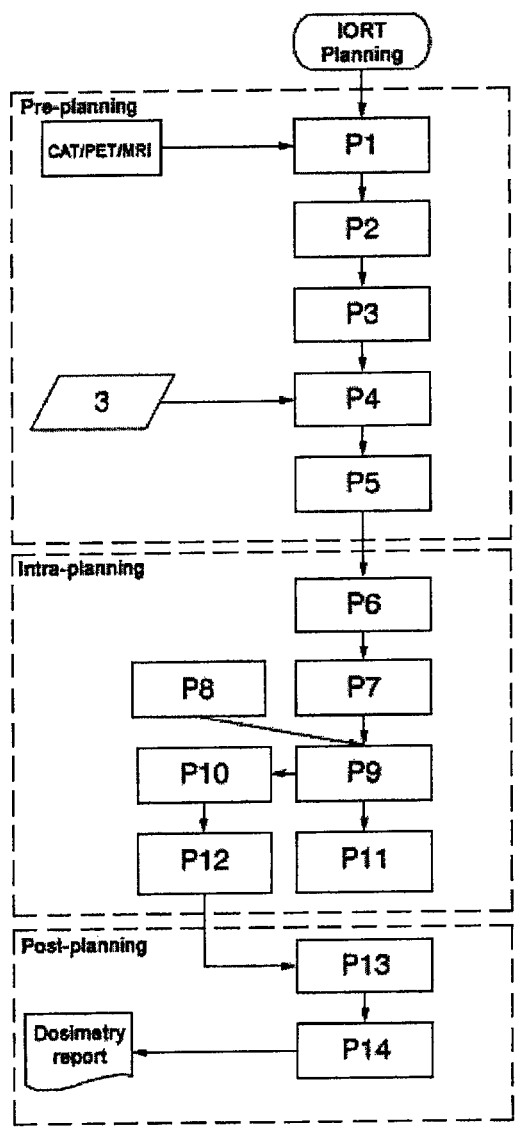
FIG. 3 finally shows the different steps of the method of the invention which allows carrying out the planning, training and recording of the system of the invention.

According to a preferred embodiment described in FIGS. 1 to 3, the planning system for intraoperative radiation therapy of the invention comprises at least one central processing unit or computer (1) for management and control of the rest of the devices, for executing the different software packages or modules responsible for generating the required simulations, for visually representing the patient's anatomy and the doses received, performing the different calculations etc.; devices responsible for representing images such as one or several monitors or screens (2), for example, in which the two-dimensional and/or three-dimensional images which the specialist can observe will be displayed, as well as peripherals responsible for gathering data relating to the actions performed by the user, simulating an actual surgical procedure, such as a computer mouse, a keyboard or haptic devices (3).

The system of the invention can further comprise a locating system (5) for locating elements in the three-dimensional space or navigator used to position the patient and the IORT applicator, typically an applicator cone (4), to adjust it to the pre-planning information and reference it to the coordinate axis of the system; devices for effectively measuring the dose (6), such as for example thermoluminescent dosimeters (TLDs) and haptic devices (3) capable of reproducing/simulating the interaction of the applicator cone (4) with the neighboring tissues in the simulated surgical procedure.

Image capture means (7) for documenting the process and checking the tumor tissue remains, and finally, a real-time image capture device (8) for complementing the preoperative image with information in the operating room, such as an ultrasound for example, can further be added to these elements.

All these elements are clearly shown in FIG. 1, in which the image of a patient's torso, representing the patient during the process, has been added.

FIG. 2 further shows a block diagram of the system of the invention in which the elements of FIG. 1 are indicated, including the images obtained from the patient prior to treatment and the output, which will be the dosimetry report of the planning performed and the application of the dose on the actual patient, the information flows between each of said blocks being indicated with arrows.

Concerning the process or method supported by the planning system of the invention, as can be seen in the flow chart of FIG. 3, the latter would generally comprise the following stages or phases:

1) Preoperative Planning or Pre-Planning:

Generally, the specialist simulates, as a result of the software of the system, the therapeutic process by balancing options and studying the optimal solution for the case in this preoperative planning phase. This phase can be performed with the control panel of the processing unit (1), the monitors or screens (2), and the haptic device (3).

The image studies which the specialist wishes to use, which are almost always a CAT scan and, optionally, a PET scan, MRI or any image study of interest, through which the system receives the necessary preoperative information of the patient will have been previously loaded.

The images are received and jointly displayed (P1) by means of the control panel of the processing unit or units (1) and the screens or monitors (2) in order to better know the extent of the pathology of the patient and to estimate the planning to be carried out.

Once the images are processed, the user selects the areas of interest for the planning (P2), whether they are areas to be protected from the radiation or targeted areas thereof.

The user performs the virtual tissue resection and separation operations (P3) on those areas of interest, and by means of the haptic device (3), the movements and operations of which are both recorded and simulated within the system as a result of the processing unit or units (1), and displayed through the screens or monitors (2), to simulate the surgical aspects which will subsequently be carried out in the process during the intraoperative phase, i.e., when actually working on the patient.

Once the tissue is arranged, the system performs a simulation (P4) of the position of the radiation therapy applicator cone (4) on the patient. The system therefore has means for calculating the amount of radiation received by each of the tissues and the specialist can thus choose the best option for the characteristics of the applicator and its position. The planner will provide feedback on the arm of the user about the collisions with virtual models of impenetrable anatomical structures (bone structures, for example) to avoid being introduced therein during the process as a result of a deformation simulation module which will allow modeling the deformation produced by the pressure of the applicator or surgical instruments on a soft tissue.

The system further has with means for instantly calculating a dose estimation which will change as the position of the applicator cone (4) is modified, and further allowing the specialist to be able to enter the prior dose information in order to make up the complete map of radiation received by the patient over a determined time period.

Finally, once the ideal position of the applicator is chosen, the system performs a precise calculation (P5) of the dose that each part of the tissue receives, paying particular attention to the previously demarcated areas of interest.

2) Intraoperative Planning or Intra-Planning:

It is generally in this phase performed in the operating room when the planning is effectively applied and adapted to the actual surgical scenario. A real-time image capture device (8), typically an ultrasound, could optionally be used in this phase.

More specifically, once the activities of pre-planning stage 1) are performed, it is necessary to calibrate the locating system or navigator (5).

The positions of the patient (P6) and of the applicator cone (4) (P7) with respect to the information before the planning are then recorded by means of the navigator (5), the applicator cone (4) and the control panel of the processing unit or units (1) and the screens or monitors (2).

Anatomical reference elements with which the specialist will relate the prior image and the actual patient will be taken to perform this activity. In the event of a real-time image capture device (8) or image capture means (7), said image will also be calibrated to refer it to the pre-planning data (P8).

Once all the elements of the system are located, the specialist will place said applicator cone (4) (P9) in the position indicated in the planning, being guided at all times by the system.

The specialist will also be able to record any deviation with respect to the initial planning which will be part of the process report.

Through the image capture means (7), the system is susceptible of gathering radiation field control images (P10) for filing in the dosimetry report, further having computer vision means to allow quantifying the tumor remains observed in the image.

Once the applicator cone (4) is prepared, in the event that the linear accelerator has an external communication module and it is appropriate in the opinion of the radiation oncologist, the system will communicate with him to provide the radiation data (P11) according to the indicated planning.

At the same time the system may take measurements (P12) by means of the devices for effectively measuring the effective radiation dose (6) through, for example, thermoluminescent dosimeters (TLDs) which is carried out to obtain control measurements.

3) Postoperative Planning or Post-Planning:

It is generally in the postoperative planning when the data gathered during the previous process are observed and the process reports are generated.

More specifically, in this phase the system allows verifying the dose (P13) that has been deposited with respect to the dose that has been planned by means of the screens or monitors (2), taking as information the measurements gathered by the devices (6) for effectively measuring the dose used or applied.

Finally, the system will generate a complete report (P14) on the process carried out by means of the processing unit or units (1) with all its steps and with the input information therein.

The invention claimed is:

1. Planning system for intraoperative radiation therapy of a patient by means of a radiation applicator cone operated by a user, the planning system comprising:
    at least one central processing unit or computer for processing image scans and for management and control and software-based communication with other devices and the user;
    one or several monitors or screens for displaying images,
    a deformation simulation module for virtually simulating a deformation produced in the patient's organs and tissues as well as a resection during a simulated process of surgery; and
    algorithms for instantly calculating a radiation dose applied by the radiation applicator cone and its distribution throughout the patient's organ or tissue concerned during the radiation therapy treatment simulation.

2. Planning system for intraoperative radiation therapy according to claim 1, wherein the peripherals comprise haptic devices.

3. Planning system for intraoperative radiation therapy according to claim 2, further comprising means capable of simulating an interaction of the radiation applicator cone with neighboring tissues in the simulated surgical procedure in the pre-operative planning stage, and of providing force feedback simulating a collision of the former with different parts of the patient's anatomy, the force feedback being provided by the haptic devices.

4. Planning system for intraoperative radiation therapy according to claim 1, further comprising a navigator for locating elements in three-dimensional space used to correlate the position of the radiation applicator cone with respect to, pre-operative planning information and adjusting it thereof.

5. Planning system for intraoperative radiation therapy according to claim 1, further comprising a real-time image capture device for complementing a preoperative image with information in the operating room.

6. Planning system for intraoperative radiation therapy according to claim 1, further comprising image capture means for documenting the process and checking tumor tissue remains by means of computer vision.

7. Planning system for intraoperative radiation therapy according to claim 1, further comprising a communication module for connection to a linear accelerator for supplying data on the dose to be administered.

8. Planning system for intraoperative radiation therapy according to claim 1, further comprising dosimeter devices for effectively measuring the dose applied.

9. Planning system for intraoperative radiation therapy according to claim 1, further comprising computer vision means for quantifying the tumor remains observed in the image obtained by the image capture means.

10. Planning method for intraoperative radiation therapy, comprising:
    loading image studies with necessary preoperative planning information of a patient;
    carrying out a preoperative planning or simulation of the therapeutic process, comprising:
        virtually simulating a deformation produced in a patient's organs and tissues as well as a resection during the simulated process of surgery;
        instantly calculating a radiation dose applied by a radiation applicator cone, and its distribution throughout the patient's organ or tissue concerned during the radiation therapy treatment simulation.

11. Planning method for intraoperative radiation therapy according to claim 10, wherein the preoperative planning stage comprises:
    jointly displaying all available images of the patient's pathology through the screens or monitors in order to estimate the planning to be carried out,
    selecting areas of interest for the planning, whether they are areas to be protected from radiation or targeted areas thereof;

performing in said areas of interest virtual tissue resection and separation operations simulating surgical aspects which will subsequently be carried out when actually working on the patient, by means of a haptic device;

simulating a position of the radiation therapy applicator cone on the patient, including feedback on an arm of the user about collisions with the virtual models of impenetrable anatomical structures and deformation produced by pressure of said applicator cone on a soft tissue, and the system instantaneously calculating the amount of radiation received by each of the tissues as the position of said applicator cone is modified; and once an ideal position of the radiation applicator cone is selected, precisely calculating a dose that each part of the tissue receives, paying particular attention to the previously demarcated areas of interest.

12. Planning method for intraoperative radiation therapy according to claim 10, wherein the intraoperative planning stage comprises:

calibrating a locating system or navigator;

recording positions of the patient and of the applicator cone with respect the preoperative planning information by taking anatomical reference elements with which the user will relate the prior image and the actual patient;

the system placing the applicator cone in the position indicated in the planning in a guided manner, the specialist also being able to record any deviation with respect to the preoperative planning information which will be part of a process report;

gathering radiation field control images and quantifying tumor remains observed in the image with computer vision means; and taking measurements by means of dosimeter devices for effectively measuring the effective radiation dose which is carried out.

13. Planning method for intraoperative radiation therapy according to claim 12, wherein additionally, while recording the positions of the patient and of the applicator cone with respect to the preoperative planning information, images obtained by means of a real-time image capture device are also recorded.

14. Planning method for intraoperative radiation therapy according to claim 10, further comprising:

performing intraoperative planning in an operating room in which the planning from the previous stage is applied and adapted to the actual surgical scenario.

15. Planning method for intraoperative radiation therapy according to claim 10, further comprising:

performing postoperative planning in which the data gathered during the previous process are observed and process reports are generated.

16. Planning method for intraoperative radiation therapy according to claim 15, wherein the postoperative planning stage comprises:

verifying a dose that has been deposited with respect to the dose that has been planned, taking as information the measurements gathered by the dosimeter devices for effectively measuring the dose used or applied; and generating a full report of the process carried out.

* * * * *